United States Patent
Dale et al.

(10) Patent No.: US 9,066,710 B2
(45) Date of Patent: Jun. 30, 2015

(54) APPARATUS AND METHOD FOR HEART VALVE REPAIR

(71) Applicant: St. Jude Medical, Cardiology Division, Inc., St. Paul, MN (US)

(72) Inventors: Theodore Paul Dale, Corcoran, MN (US); Richard J. Olson, Blaine, MN (US); Benjamin E. Morris, Jeffersonville, IN (US); John Miser, Crestwood, KY (US); Aleksandr I. Nadein, Louisville, KY (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 133 days.

(21) Appl. No.: 13/790,852

(22) Filed: Mar. 8, 2013

(65) Prior Publication Data
US 2014/0114403 A1    Apr. 24, 2014

Related U.S. Application Data

(60) Provisional application No. 61/716,277, filed on Oct. 19, 2012.

(51) Int. Cl.
*A61B 17/10* (2006.01)
*A61B 17/00* (2006.01)
(Continued)

(52) U.S. Cl.
CPC ....... *A61B 17/00234* (2013.01); *A61B 17/0644* (2013.01); *A61B 17/068* (2013.01);
(Continued)

(58) Field of Classification Search
CPC ........... A61B 17/07207; A61B 17/068; A61B 17/115; A61B 17/1285; A61B 17/0487; A61B 17/128; A61B 2017/0488; A61F 2/2472

USPC ......... 606/139, 142, 143, 205, 206, 207, 208; 623/2.11; 227/175.1, 176.1, 179.1
See application file for complete search history.

(56) References Cited

U.S. PATENT DOCUMENTS 5,156,608 A * 10/1992 Troidl et al. .................. 606/142
5,601,573 A *  2/1997 Fogelberg et al. ............ 606/143
(Continued)

FOREIGN PATENT DOCUMENTS

AU   2002300522 B2   1/2007
WO      9620749 A1   7/1996
(Continued)

OTHER PUBLICATIONS

Merriam-Webster definition of "fabric" as accessed on Dec. 17, 2014; http://www.merriam-webster.com/dictionary/fabric.
(Continued)

*Primary Examiner* — Jonathan W Miles
(74) *Attorney, Agent, or Firm* — Lerner, David, Littenberg, Krumholz & Mentlik, LLP

(57) ABSTRACT

A device for transcatheter gathering of tissue of a heart valve leaflet may include an elongated tube, a capture tool moveable in the tube between a retracted position and an extended position, a tissue support located within a distal portion of the tube, and a clamping member pivotable in the tube between an open position spaced from the tissue support and a closed position adjacent the tissue support. The clamping member may have a flattened clamping portion and a C-shaped portion that defines a pocket therein. An open side of the C-shaped portion may face the tissue support. The capture tool and the clamping member may be operable to gather and clamp tissue between the tissue support and the clamping member, such that the clamped tissue has a gathered configuration. The device may also include a releasable clip adapted to hold the clamped tissue in the gathered configuration.

20 Claims, 4 Drawing Sheets

(51) Int. Cl.
  A61B 17/064 (2006.01)
  A61B 17/068 (2006.01)
  A61B 17/122 (2006.01)
  A61B 17/29 (2006.01)

(52) U.S. Cl.
  CPC ... *A61B17/1227* (2013.01); *A61B 2017/00243* (2013.01); *A61B 2017/00292* (2013.01); *A61B 2017/00349* (2013.01); *A61B 2017/00353* (2013.01); *A61B 2017/00367* (2013.01); *A61B 2017/00477* (2013.01); *A61B 2017/00867* (2013.01); *A61B 2017/0645* (2013.01); *A61B 2017/0649* (2013.01); *A61B 2017/2927* (2013.01); *A61B 2017/00783* (2013.01)

(56) References Cited

U.S. PATENT DOCUMENTS

| | | | |
|---|---|---|---|
| 5,749,879 A | 5/1998 | Middleman et al. | |
| 5,921,993 A | 7/1999 | Yoon | |
| 6,440,152 B1 | 8/2002 | Gainor et al. | |
| 6,569,182 B1 | 5/2003 | Balceta et al. | |
| 6,752,813 B2 | 6/2004 | Goldfarb et al. | |
| 6,945,978 B1 | 9/2005 | Hyde | |
| 7,011,669 B2 | 3/2006 | Kimblad | |
| 7,464,712 B2 | 12/2008 | Oz et al. | |
| 7,569,062 B1 | 8/2009 | Kuehn et al. | |
| 7,758,595 B2 | 7/2010 | Allen et al. | |
| 8,777,966 B2 * | 7/2014 | Dale et al. | 606/142 |
| 2001/0016750 A1 | 8/2001 | Malecki et al. | |
| 2002/0013571 A1 | 1/2002 | Goldfarb et al. | |
| 2002/0107531 A1 | 8/2002 | Schreck et al. | |
| 2003/0093071 A1 | 5/2003 | Hauck et al. | |
| 2004/0039442 A1 | 2/2004 | St. Goar et al. | |
| 2004/0181238 A1 | 9/2004 | Zarbatany et al. | |
| 2004/0193185 A1 * | 9/2004 | McBrayer | 606/142 |
| 2005/0090837 A1 * | 4/2005 | Sixto et al. | 606/139 |
| 2005/0096671 A1 | 5/2005 | Wellman et al. | |
| 2005/0125011 A1 | 6/2005 | Spence et al. | |
| 2005/0143763 A1 * | 6/2005 | Ortiz et al. | 606/153 |
| 2005/0149072 A1 | 7/2005 | DeVries et al. | |
| 2005/0177176 A1 * | 8/2005 | Gerbi et al. | 606/139 |
| 2005/0251161 A1 * | 11/2005 | Saadat et al. | 606/153 |
| 2006/0122633 A1 | 6/2006 | To et al. | |
| 2006/0173422 A1 | 8/2006 | Reydel et al. | |
| 2007/0049952 A1 | 3/2007 | Weiss | |
| 2007/0102474 A1 * | 5/2007 | Shelton et al. | 227/175.1 |
| 2007/0102475 A1 * | 5/2007 | Ortiz et al. | 227/175.2 |
| 2007/0142846 A1 | 6/2007 | Catanese et al. | |
| 2007/0162056 A1 | 7/2007 | Gerbi et al. | |
| 2007/0197858 A1 | 8/2007 | Goldfarb et al. | |
| 2007/0225734 A1 | 9/2007 | Bell et al. | |
| 2008/0294175 A1 | 11/2008 | Bardsley et al. | |
| 2008/0300624 A1 | 12/2008 | Schwemberger et al. | |
| 2009/0062852 A1 | 3/2009 | Marino | |
| 2009/0118744 A1 | 5/2009 | Wells et al. | |
| 2009/0125038 A1 * | 5/2009 | Ewers et al. | 606/142 |
| 2009/0149870 A1 | 6/2009 | Jugenheimer et al. | |
| 2011/0077668 A1 | 3/2011 | Gordon et al. | |
| 2011/0087242 A1 * | 4/2011 | Pribanic et al. | 606/142 |
| 2011/0114700 A1 | 5/2011 | Baxter, III et al. | |
| 2011/0230897 A1 | 9/2011 | Palermo et al. | |
| 2011/0313432 A1 * | 12/2011 | Miles et al. | 606/142 |
| 2012/0226291 A1 * | 9/2012 | Malizia et al. | 606/143 |
| 2013/0046332 A1 | 2/2013 | Jones et al. | |
| 2014/0039607 A1 * | 2/2014 | Kovach | 623/2.11 |

FOREIGN PATENT DOCUMENTS

| | | | |
|---|---|---|---|
| WO | 9900059 A1 | 1/1999 | |
| WO | 0128432 A1 | 4/2001 | |
| WO | 0139672 A2 | 6/2001 | |
| WO | 0182847 A2 | 11/2001 | |
| WO | 0200121 A1 | 1/2002 | |
| WO | 03049619 A2 | 6/2003 | |
| WO | 2006039199 A2 | 4/2006 | |
| WO | 2007027451 A2 | 3/2007 | |
| WO | 2008068756 A2 | 6/2008 | |
| WO | 2008121738 A2 | 10/2008 | |
| WO | 2009087592 A2 | 7/2009 | |
| WO | 2010094896 A1 | 8/2010 | |
| WO | 2011053673 A1 | 5/2011 | |
| WO | 2012087724 A1 | 6/2012 | |
| WO | 2012106398 A1 | 8/2012 | |
| WO | 2013019415 A1 | 2/2013 | |
| WO | 2013116617 A1 | 8/2013 | |
| WO | 2014022464 A1 | 2/2014 | |

OTHER PUBLICATIONS

International Search Report and Written Opinion for Application No. PCT/US2013/052843 dated Oct. 11, 2013.
International Search Report and Written Opinion for Application No. PCT/US2013/052838 dated Oct. 11, 2013.
International Search Report and Written Opinion for Application No. PCT/US2013/052822 dated Jan. 21, 2014.
International Preliminary Report on Patentability for Application No. PCT/US2012/023437 dated Aug. 6, 2013.
International Search Report for Application No. PCT/US2013/023077 dated May 14, 2013.
International Search Report and Written Opinion for Application No. PCT/US2013/023082 dated Oct. 1, 2013.
International Search Report and Written Opinion for Application No. PCT/US2013/024304 dated Jul. 5, 2013.
International Search Report for Application No. PCT/US2013/052832 dated Jan. 15, 2014.
International Search Report and Written Opinion for Application No. PCT/US2013/065360 dated Apr. 23, 2014.
International Search Report for Application No. PCT/US2012/023437 dated Apr. 24, 2012.

* cited by examiner

APPARATUS AND METHOD FOR HEART VALVE REPAIR

CROSS-REFERENCE TO RELATED APPLICATION

The present application claims the benefit of the filing date of U.S. Provisional Patent Application No. 61/716,277 filed Oct. 19, 2012, the disclosure of which is hereby incorporated herein by reference.

BACKGROUND OF THE INVENTION

The present invention is related to heart valve repair, and more particularly to devices, systems, and methods for transcatheter repair of a heart valve leaflet.

Properly functioning heart valves can maintain unidirectional blood flow in the circulatory system by opening and closing, depending on the difference in pressure on each side of the valve. The two atrioventricular valves (mitral and tricuspid valves) are multicusped valves that prevent backflow from the ventricles into the atria during systole. They are anchored to the wall of the ventricle by chordae tendinae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendinae may stretch and thus become too long, or the chordae tendinae may be broken. As a result, the valve does not close normally. As a result of being stretched, the unsupported valve leaflet bulges back, or "prolapses," into the left atrium like a parachute. Thus, as the ventricle contracts, the abnormal leaflet may be propelled backwards, beyond its normal closure line into the left atrium, thereby allowing blood to return back into the left atrium and the lungs.

Mitral valve prolapse causes mitral regurgitation. Isolated posterior leaflet prolapse of the human heart mitral valve, i.e. prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods may be invasive to the patient and may require an extended recovery period.

There therefore is a need for further improvements to the current techniques for treating heart valve leaflet prolapse. Among other advantages, the present invention may address one or more of these needs.

Patents relevant to devices, systems, and methods for transcatheter repair of heart valve leaflets include U.S. Pat. Nos. 6,752,813, 7,464,712, and 7,758,595.

BRIEF SUMMARY OF THE INVENTION

Devices and methods for transcatheter gathering of heart valve leaflet tissue are disclosed. A device for transcatheter gathering of tissue of a heart valve leaflet may include an elongated tube extending in a longitudinal direction, a capture tool moveable in the tube between a retracted position and an extended position, a tissue support located within a distal portion of the tube, and a clamping member pivotable in the tube between an open position spaced from the tissue support and a closed position adjacent the tissue support.

The clamping member may have a flattened clamping portion and a C-shaped portion that defines a pocket therein. An open side of the C-shaped portion may face the tissue support. The capture tool and the clamping member may be operable to gather and clamp tissue of the heart valve leaflet between the tissue support and the clamping member, such that the clamped tissue has a gathered configuration. The device may also include a releasable clip adapted to be applied to the clamped tissue for holding the clamped tissue in the gathered configuration, and a retaining arm moveable between a distal position for retaining the clip and a proximal position for releasing the clip for application to the clamped tissue.

A distal portion of the clamping member may have a fork shape. The distal portion of the clamping member may have two tines having respective ends that are spaced apart from one another by an internal gap. The device may also include an operating handle having an actuating member adapted to control pivoting of the clamping member between the open and closed positions. The device may include two releasable clips adapted to be applied to the clamped tissue for holding the clamped tissue in the gathered configuration. Each clip may be biased from an open condition to a clamping condition. The retaining arm in the distal position may hold the clips in the open condition. The retaining arm in the proximal position may release the clips for application to the clamped tissue.

The tissue support may include first, second, and third bodies spaced apart in the longitudinal direction. When the clips are held in the open condition by the retaining arm, a first one of the clips may be located between the first and second bodies, and a second one of the clips may be located between the second and third bodies. Movement of the retaining arm from the distal position to an intermediate position may release a first one of the clips. Movement of the retaining arm from the intermediate position to the proximal position may release a second one of the clips. The device may also include an operating handle having an actuating member adapted to control movement of the retaining arm between the distal position and the proximal position.

The device may include two releasable clips adapted to be applied to the clamped tissue for holding the clamped tissue in the gathered configuration. A first actuation of the actuating member may move the actuating member from the distal position to an intermediate position to release a first one of the clips. A second actuation of the actuating member may move the actuating member from the intermediate position to the proximal position to release a second one of the clips. The capture tool may include a grasping wire slidably disposed in a containment tube. A distal portion of the grasping wire may be adapted to change from a linear shape to a hook shape when the distal portion of the grasping wire is extended out from the containment tube.

Another device for transcatheter gathering of tissue of a heart valve leaflet may include an elongated tube extending in a longitudinal direction, a capture tool moveable in the tube between a retracted position and an extended position, a tissue support located within a distal portion of the tube, and a clamping member pivotable in the tube between an open position spaced from the tissue support and a closed position adjacent the tissue support. The capture tool and the clamping member may be operable to gather and clamp tissue of the heart valve leaflet between the tissue support and the clamping member, such that the clamped tissue has a gathered configuration.

The device may also include a releasable clip adapted to be applied to the clamped tissue for holding the clamped tissue in the gathered configuration, and a retaining arm moveable between a distal position for retaining the clip and a proximal position for releasing the clip for application to the clamped tissue. The device may also include an operating handle having a distal portion that is affixed to the elongated tube and a proximal portion that is rotatable relative to the distal portion about a longitudinal axis of the handle.

The operating handle may have an actuating member movable between a first position and a second position. The proximal portion of the operating handle may be rotationally locked to the distal portion of the operating handle when the actuating member is in the first position. The proximal portion of the operating handle may be released for rotation relative to the distal portion of the operating handle when the actuating member is in the second position. The actuating member may include a spring element that biases the actuating member to the first position.

The device may include two releasable clips adapted to be applied to the clamped tissue for holding the clamped tissue in the gathered configuration. Movement of the retaining arm from the distal position to an intermediate position may release a first one of the clips. Movement of the retaining arm from the intermediate position to the proximal position may release a second one of the clips.

A transcatheter method of gathering tissue of first and second heart valve leaflets may include inserting an elongated catheter assembly to a position adjacent the first heart valve leaflet. The catheter assembly may extend from an operating handle in a longitudinal direction and may include a capture tool moveable between a retracted position and an extended position, a tissue support, a clamping member pivotable between an open position spaced from the tissue support and a closed position adjacent the tissue support, and a retaining arm moveable between a distal position for retaining two clips and a proximal position for releasing the clips. The operating handle may have a distal portion that is affixed to the catheter assembly and a proximal portion that is rotatable relative to the distal portion about a longitudinal axis of the handle.

The method may also include moving the capture tool from the retracted position to the extended position, and pivoting the clamping member from the closed position to the open position adjacent the first heart valve leaflet, such that a distal portion of the clamping member moves laterally away from the tissue support in a direction transverse to the longitudinal direction. The method may also include manipulating the catheter assembly so that tissue of the first heart valve leaflet is positioned between the tissue support and the clamping member, and partially retracting the capture tool from the extended position toward the retracted position to gather an additional amount of tissue of the first heart valve leaflet between the tissue support and the clamping member.

The method may also include pivoting the clamping member from the open position toward the closed position so as to clamp a substantial portion of the gathered tissue of the first heart valve leaflet between the tissue support and the clamping member, such that the distal portion of the clamping member moves laterally toward the tissue support in the direction transverse to the longitudinal direction, the clamped tissue having a gathered configuration. The method may also include moving the retaining arm from the distal position to an intermediate position to apply a first one of the clips from the catheter assembly to the clamped tissue so as to hold the clamped tissue substantially in the gathered configuration, rotating the catheter assembly and the distal portion of the operating handle relative to the proximal portion of the operating handle, and moving the retaining arm from the intermediate position to the proximal position to apply a second one of the clips from the catheter assembly to the tissue of the second heart valve leaflet.

Each clip may be biased from an open condition to a clamping condition, and the retaining arm may hold the clips in the open condition. The step of moving the retaining arm from the distal position to the proximal position may release the clips for movement to the clamping condition. The operating handle may have an actuating member moveable in opposite directions. The step of pivoting the clamping member from the closed position to the open position may include moving the actuating member in a first one of the opposite directions.

A transcatheter method of gathering tissue of a heart valve leaflet may include inserting an elongated catheter assembly to a position adjacent the heart valve leaflet. The catheter assembly may extend in a longitudinal direction and may include a capture tool moveable between a retracted position and an extended position, a tissue support, a clamping member pivotable between an open position spaced from the tissue support and a closed position adjacent the tissue support, and a retaining arm moveable between a distal position for retaining two clips and a proximal position for releasing the clips.

The method may also include moving the capture tool from the retracted position to the extended position, and pivoting the clamping member from the closed position to the open position adjacent the heart valve leaflet, such that a distal portion of the clamping member moves laterally away from the tissue support in a direction transverse to the longitudinal direction. The method may also include manipulating the catheter assembly so that tissue of the heart valve leaflet is positioned between the tissue support and the clamping member, and partially retracting the capture tool from the extended position toward the retracted position to gather an additional amount of tissue of the heart valve leaflet between the tissue support and the clamping member.

The method may also include pivoting the clamping member from the open position toward the closed position so as to clamp a substantial portion of the gathered tissue of the heart valve leaflet between the tissue support and the clamping member, such that the distal portion of the clamping member moves laterally toward the tissue support in the direction transverse to the longitudinal direction, the clamped tissue having a gathered configuration. The method may also include moving the retaining arm from the distal position to an intermediate position to apply a first one of the clips from the catheter assembly to the clamped tissue so as to hold the clamped tissue substantially in the gathered configuration, and moving the retaining arm from the intermediate position to the proximal position to apply a second one of the clips from the catheter assembly to the clamped tissue.

The catheter assembly may also include an operating handle having an actuating member actuatable in a first direction. The step of moving the retaining arm from the distal position to the intermediate position may be performed by actuating the actuating member a first time. The step of moving the retaining arm from the intermediate position to the proximal position may be performed by actuating the actuating member a second time. The capture tool may include a grasping wire slidably disposed in a containment tube. The method may also include sliding a distal portion of the grasping wire out from the containment tube so that the distal portion of the grasping wire changes from a linear shape to a hook shape.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

DETAILED DESCRIPTION

As used herein, the terms "proximal" and "distal" are to be taken as relative to a user (e.g., a surgeon or an interventional cardiologist) using the disclosed transcatheter devices. "Proximal" is to be understood as relatively close to the user and "distal" is to be understood as relatively farther away from the user. The invention will be described in connection with the repair of a mitral valve leaflet, but it may be useful in the repair of other types of cardiac valves or in the gathering and clamping of other types of loose body tissue.

Figure 1:
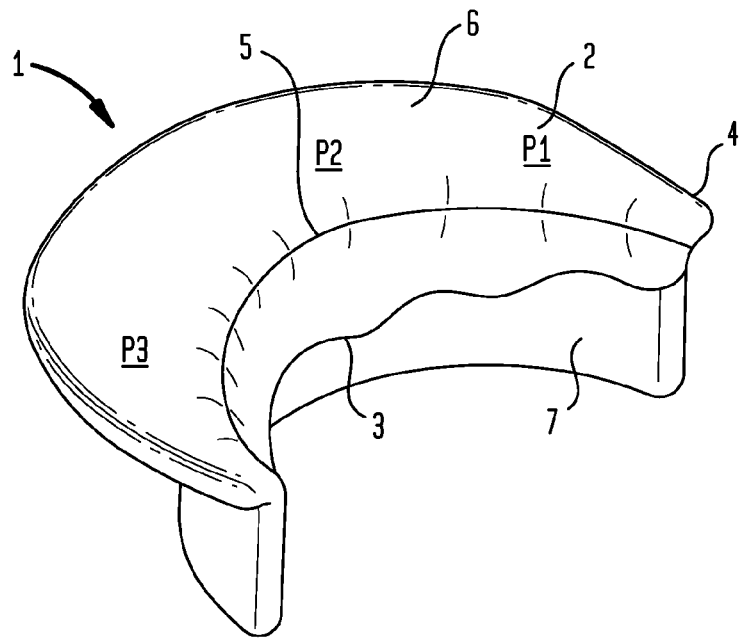
FIG. 1 is a diagrammatic perspective view of the posterior leaflet of a mitral valve.

Referring to FIG. 1, an exemplary mitral valve 1 includes a posterior leaflet 2 and an anterior leaflet 3. The leaflets 2 and 3 extend from an annulus 4 to a coaption line 5 where the leaflets meet. The posterior leaflet 2 has an upper portion 6 that is generally perpendicular to the direction of blood flow through the valve 1 and extends between the annulus and the coaption line 5. Additionally, the posterior leaflet 2 has a lower portion 7 that is generally parallel to the direction of blood flow through the valve 1 and extends below the coaption line 5. The posterior leaflet 2 has three scalloped portions P1, P2, and P3, any of which may include a portion that is billowed, loose, or floppy, and therefore be the cause of a prolapse condition of the valve. The inventive devices, systems, and methods described herein may be adapted to repair such a billowed, loose, or floppy portion of the posterior leaflet 2 or the anterior leaflet 3.

Figure 2:
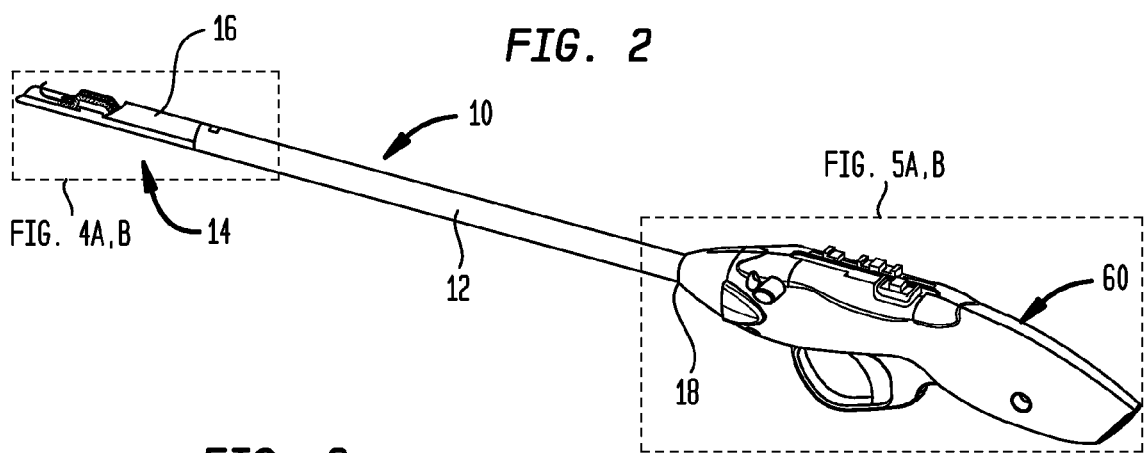
FIG. 2 is a perspective view of a device for transcatheter gathering of heart valve leaflet tissue.

Referring to FIG. 2, an exemplary device 10 for transcatheter gathering of heart valve leaflet tissue includes an elongated catheter assembly 12 adapted to be inserted through the apex of a human heart so that a distal portion 14 of the catheter assembly may reach the patient's mitral valve 1 for repair thereof. The device 10 further includes a handle at the proximal end 18 of the catheter assembly 12 for controlling the operation of the device.

Figure 3:
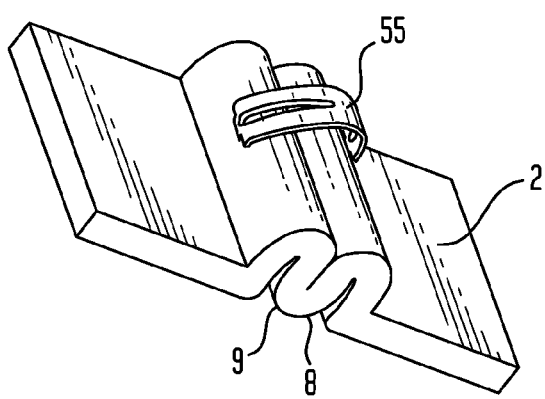
FIG. 3 is a diagrammatic view of a clip deployed on the posterior mitral valve leaflet of FIG. 1.

As will be described more fully below, the device 10 may be used to capture tissue of the posterior leaflet 2 or the anterior leaflet 3 and form a W-shaped pleat 8 (FIG. 3) therein, and to secure the captured tissue by embedding one or more clips 55 therein. By forming a W-shaped pleat 8, most or all of the portion of the posterior leaflet 2 or anterior leaflet 3 that is billowed, loose, or floppy may be gathered and tightened.

Figure 4A:
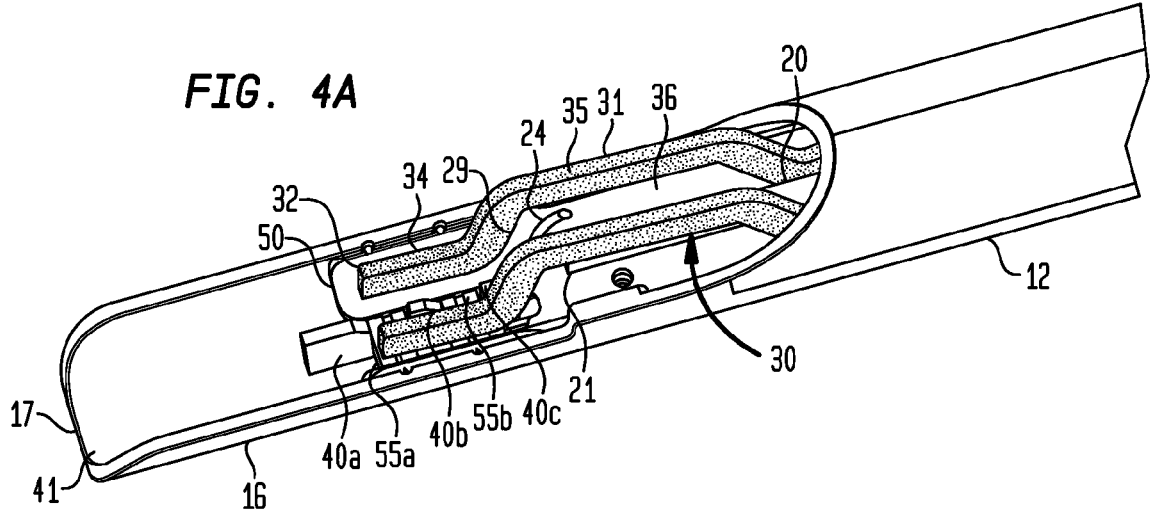
FIG. 4A is a perspective view of the distal portion of the device of FIG. 2, shown with the fork in the initial position.
Figure 4B:
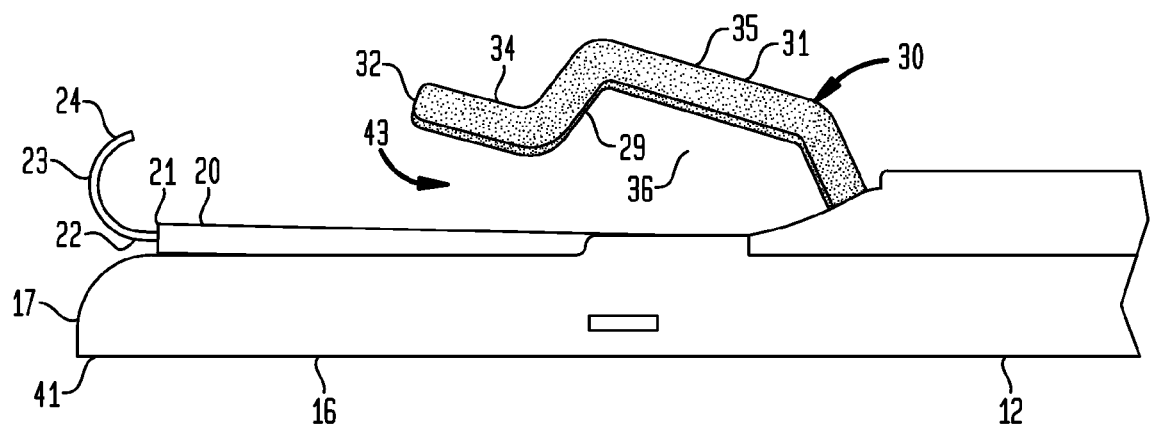
FIG. 4B is a side view of the distal portion of the device of FIG. 2, shown with the fork in the support position.

Referring to FIGS. 4A and 4B, the catheter assembly includes a containment tube 20 disposed within an outer tube 16 and longitudinally slidable therein between a proximal retracted position (FIG. 4A) and a distal deployed position (FIG. 4B) in which a distal tip 21 of the containment tube is moved toward the distal edge 17 of the outer tube. In a particular embodiment, the outer tube 16 may be made of one or more echogenic materials, so that the outer tube may be more easily visualized inside a patient using three-dimensional echocardiography.

The catheter assembly 12 further includes a capture tool in the form of a grasping wire 22 that is longitudinally slidable within the containment tube 20 between a retracted position substantially entirely within the lumen of the containment tube (not shown), and a deployed position in which a distal portion 23 of the grasping wire protrudes from the distal tip of the containment tube (FIGS. 4A and 4B). The grasping wire 22 may have a linear configuration when fully retracted within the containment tube 20 and the distal portion 23 thereof may assume the shape of a hook 24 when deployed from the containment tube. In that regard, the grasping wire 22 may be formed from a memory metal or a strong, resilient metal or polymer that will cause the hook 24 to form automatically when deployed.

Figure 4C:
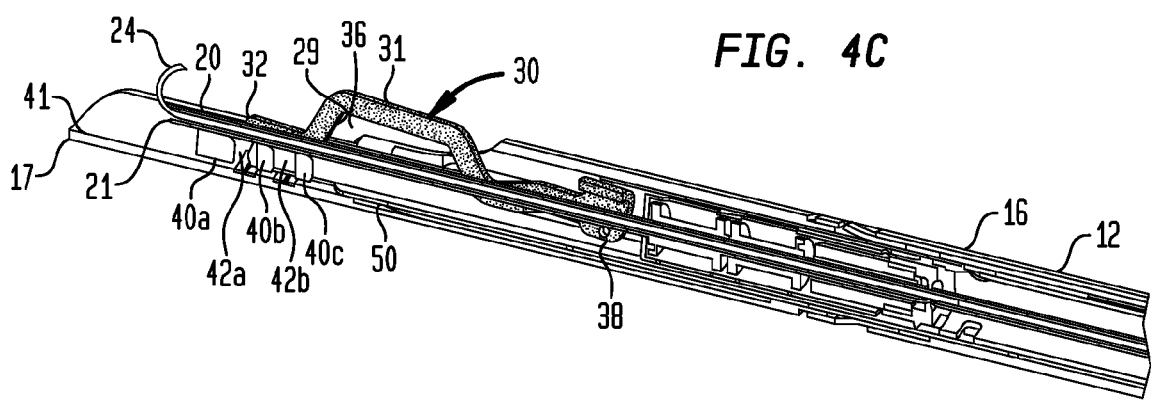
FIG. 4C is a longitudinal cross-sectional view of the distal portion of the device of FIG. 2.
Figure 4D:
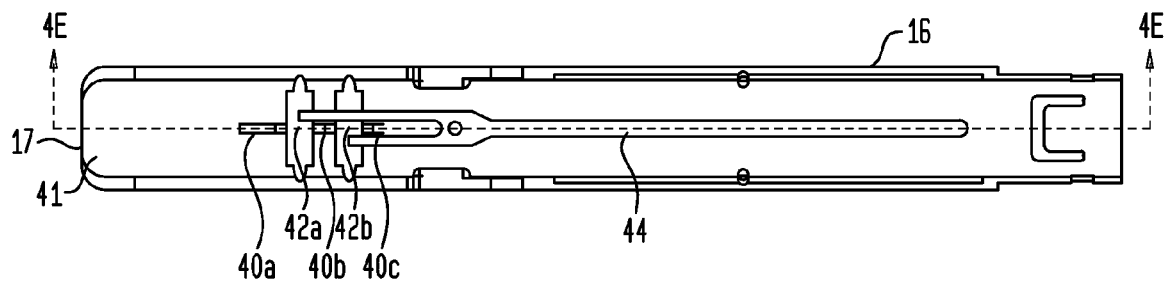
FIG. 4D is a top plan view of the distal portion of the outer tube of FIG. 4A.
Figure 4E:
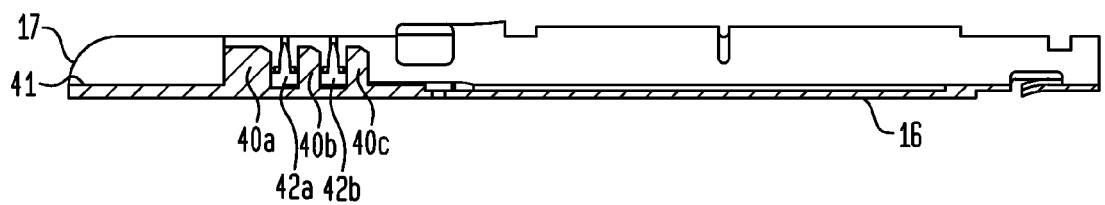
FIG. 4E is a longitudinal cross-sectional view taken along line 4E-4E of FIG. 4D.
Figure 4F:
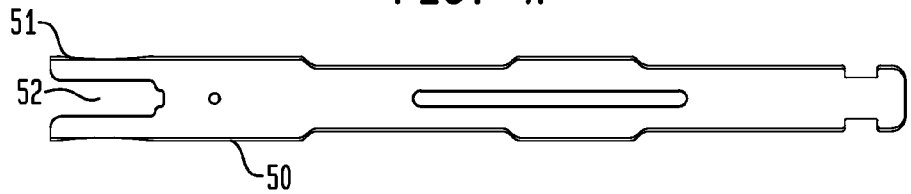
FIG. 4F is a top plan view of the retaining arm of FIG. 4A.
Figure 4G:
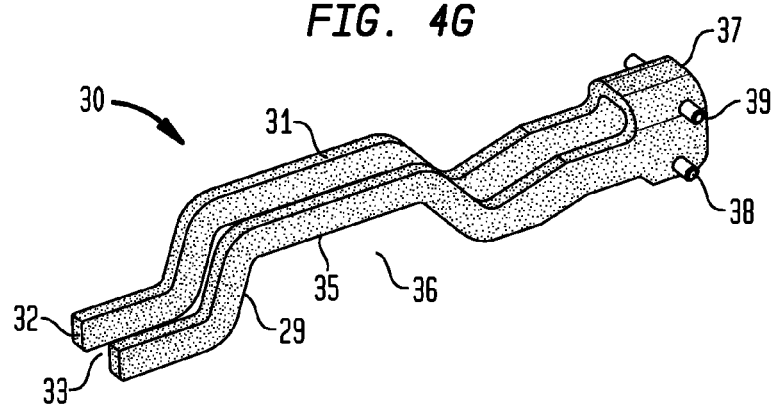
FIG. 4G is a perspective view of the fork of FIG. 4A.

The catheter assembly 12 further includes a clamping member in the form of a fork 30 that is pivotable relative to the outer tube 16 between a tissue-capturing position (FIG. 4A) and an open position (FIG. 4B). The fork 30 includes two tines 31 having respective ends 32, the tines being spaced apart from one another by an internal gap 33 (FIG. 4G). The tines 31 of the fork 30 may each have a flattened clamping portion 34 and a C-shaped portion 35 that defines a pocket 36 therein.

The concave shape of the C-shaped portion 35 provides additional space between the tines 31 of the fork 30 and the closed side 41 of the outer tube 16 for gathering of excess leaflet tissue. Furthermore, because the tines 31 include a concave C-shaped portion 35 rather than being generally straight, the C-shaped portion may help prevent tissue captured in the pocket 36 from sliding out from underneath the tines as the fork 30 clamps tissue against the anvil 40. The presence within the C-shaped portion 35 of a generally proximal-facing surface 29 may help interfere with and retain tissue in the pocket 36 that may otherwise begin to slide out from the space 43 as the fork 30 clamps tissue against the anvil 40.

The fork 30 further includes a base 37 and a pivot pin 38 and an actuation pin 39 extending through the base, the pins being orientated substantially orthogonal to the longitudinal direction in which the tines generally extend. The pivot pin 38 may be coupled to the outer tube 16 such that the pivot pin is translationally fixed to the outer tube, but the fork 30 can pivot about the pivot pin relative to the outer tube. The actuation pin 39 can be coupled to the handle 60 by a linkage (not shown) as described below, such that the linkage can be acutated to translate the actuation pin in a longitudinal direction of the outer tube 16 to selectively pivot the fork 30 about the pivot pin 38, thereby moving the fork between the tissue-capturing and open positions.

At its distal end 17, the outer tube 16 has an open side that provides clearance for the fork 30 to move away from the closed side 41 of the outer tube. A tissue support in the form of an anvil 40 (FIGS. 4A, 4C, 4D, and 4E) is mounted on the closed side 41 of the outer tube 16 so as to lie between the closed side 41 and the containment tube 20 when the containment tube is in the deployed position. The anvil 40 has a distal portion 40a, an intermediate portion 40b, and a proximal portion 40c, with a distal gap 42a defined between the distal and intermediate portions, and a proximal gap 42b defined between the proximal and intermediate portions. The widths of the portions 40a, 40b, and 40c are such that the anvil 40 may be received in the space 33 between the tines 31 of the fork 30 during the use of the device 10 to repair the valve leaflet.

The catheter assembly 12 further includes a retaining arm 50 (FIGS. 4A and 4F) disposed within the outer tube 16 and longitudinally slidable therein between an initial position (FIG. 4A) and a retracted position (not shown). The retaining arm 50 includes a pair of fingers 51 separated by an elongated slot 52. The slot 52 is sized to receive the anvil 40 when the retaining arm 50 is in the initial position shown in FIG. 4A. In this initial position, the fingers 51 lie on either side of the anvil 40 and engage first and second clips 55a and 55b disposed within the respective distal and proximal gaps 42a and 42b, holding them in place against the closed side 41 of the outer tube 16. The retraction of the retaining arm 50 releases the clips 55a and 55b for application to tissue.

Figure 4H:
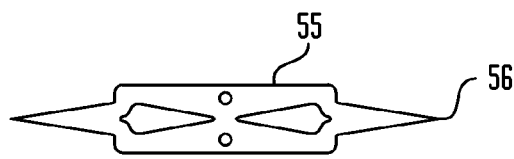
FIG. 4H is a plan view of a clip for use with the device of FIG. 2, shown in a flat condition.
Figure 4I:
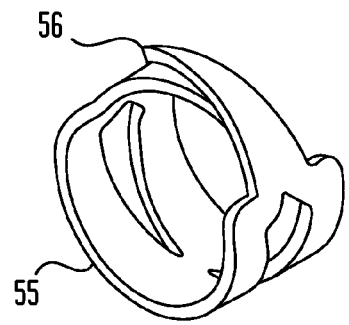
FIG. 4I is a perspective view of the clip of FIG. 4H, shown in a closed condition.

Each clip 55 (FIGS. 4H and 4I) may be made of a memory metal and may be biased to curl into a substantially round configuration (FIG. 4I) when the retaining arm 50 is retracted proximally and the fingers 51 no longer overlie the clip. A prong 56 at each end of each clip 55 is adapted to become embedded in the leaflet tissue when the clip is deployed.

Figure 5A:
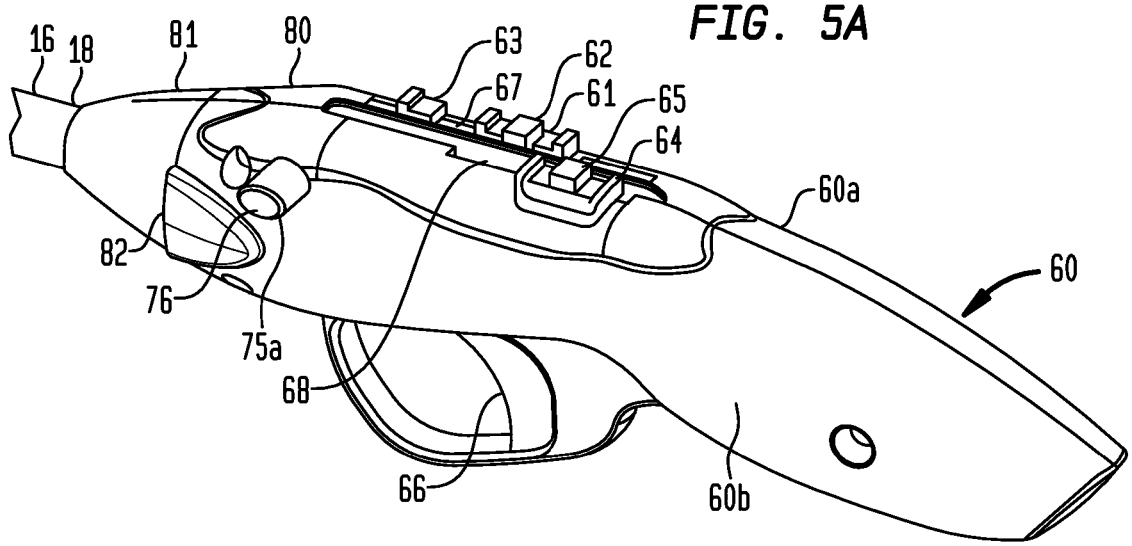
FIGS. 5A and 5B are a perspective view and a side view, respectively, of the handle of FIG. 2.
Figure 5B:
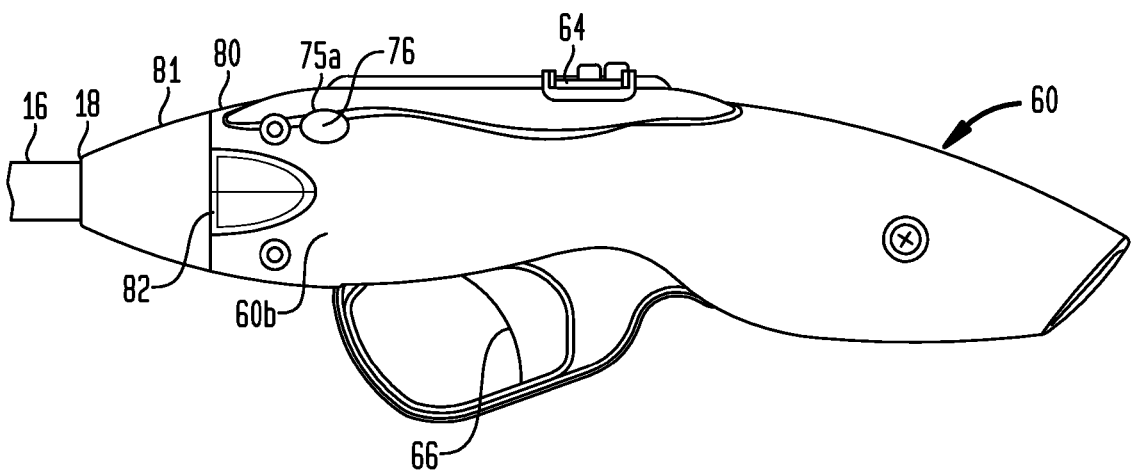

Referring now to FIGS. 5A and 5B, the handle 60 of the device 10 includes a first button 61, a second button 63, a third button 64, and a fourth button 66 for controlling the operation of the containment tube 20, the grasping wire 22, the fork 30, and the retaining arm 50, respectively.

The first button 61 and the second button 63 are mounted in a single track 67 and are moveable longitudinally relative to the handle 60 and relative to one another. The first button 61 is operatively connected to the containment tube 20, such that sliding movement of the first button in a proximal or distal direction results in a corresponding sliding movement of the containment tube. A locking feature 62 associated with the first button 61 can be actuated to lock or unlock the position of the first button within the track 67. The second button 63 is operatively connected to the grasping wire 22, such that sliding movement of the second button in a proximal or distal direction results in a corresponding sliding movement of the grasping wire.

The containment tube 20 and the grasping wire 22 may be moved together by the simultaneous movement of the first and second buttons 61 and 63. Alternatively, the containment tube 20 and the grasping wire 22 may be moved independently of one another by moving one of the buttons 61 and 63 while the other button remains stationary. For example, sliding the second button 63 distally while the first button 61 remains stationary advances the grasping wire 22 out from the containment tube 20, resulting in deployment of the hook 24.

The third button 64 is mounted in a track 68 and moveable longitudinally relative to the handle 60 for controlling the pivoting of the fork 30 relative to the outer tube 16. The third button 64 is attached to the actuation pin of the fork 30 through a linkage (not shown) extending through the handle 60 and the outer tube. When the third button 64 is moved from the proximal position shown in FIG. 5A to a distal position (not shown), the fork 30 pivots about the pivot pin 38 so as to be moved from the tissue-capturing position (FIG. 4A) to the open position (FIG. 4B). Movement of the third button 64 from the distal position to the proximal position moves the fork 30 from the open position to the tissue-capturing position. A locking feature 65 associated with the third button 64 can be actuated to lock or unlock the position of the first button within the track 68.

The fourth button 66 has a trigger shape and is movable generally in the direction of the longitudinal axis of the handle for controlling the movement of the retaining arm 50 relative to the outer tube 16. A spring (not shown) biases the fourth button 66 to return to its initial position (FIGS. 5A and 5B) after the button has been actuated. A first actuation of the fourth button 66 may retract the retaining arm 50 proximally so that the fingers 51 are moved proximally of the first clip 55a, thereby releasing the first clip for deployment. A second actuation of the fourth button 66 may retract the retaining arm 50 further proximally so that the fingers 51 are moved proximally of the second clip 55b, thereby releasing the second clip for deployment.

The handle 60 may include a distal portion 81 that is affixed to the outer tube 16, and a proximal portion 80 that is normally locked in a fixed position relative to the distal portion, but that can be released for rotation relative to the distal portion about the longitudinal axis of the handle. The handle 60 may include one or a pair of decoupling buttons 82 that, when depressed, can release the proximal portion 80 from the distal portion 81 of the handle so that they can be rotated relative to one another. The decoupling buttons 82 are movable along an axis transverse to the longitudinal axis of the handle between a depressed position towards the longitudinal axis of the handle (not shown) and an extended position away from the longitudinal axis of the handle (FIG. 5A). The decoupling buttons 82 include a spring element (not shown) that biases the decoupling buttons to the extended position.

Figure 5C:
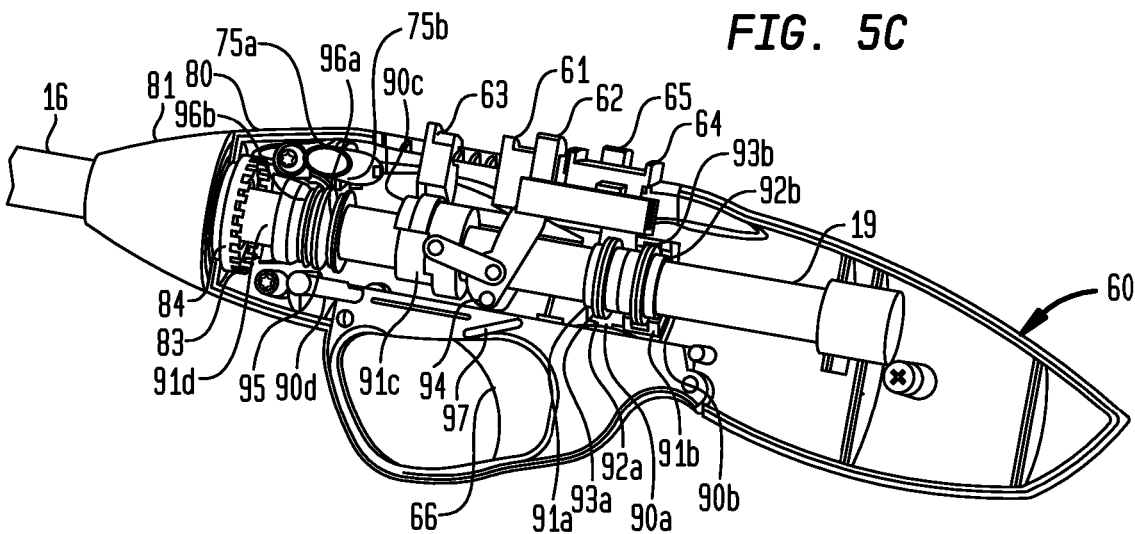
FIG. 5C is a side view of the handle of FIG. 2, with a portion of the housing removed to illustrate the internal components thereof.

The decoupling buttons 82 have engagement portions (not shown) that are configured to engage crenellations 83 of a ring 84 (FIG. 5C) that is affixed to the proximal portion 80 of the handle 60. To free the proximal portion 80 and the distal portion 81 of the handle 60 so that they can be rotated relative to one another, the user may depress the decoupling buttons 82 into the handle against the bias of the spring elements, which disengages the engagement portions of the decoupling buttons from the crenellations 83. To fix the rotational positions of the proximal portion 80 and the distal portion 81 of the handle 60 relative to one another, the user may release the decoupling buttons 82, so that the spring elements return the decoupling buttons to the extended position and so that the engagement portions of the decoupling buttons engage the crenellations 83. When the decoupling buttons 82 are released, if the engagement portions of the decoupling buttons are not aligned so as to extend into the crenellations 83, the proximal portion 80 and the distal portion 81 may be rotated relative to one another until the engagement portions are properly aligned, and the spring elements will then push the engagement portions into engagement with the crenellations.

The handle 60 further includes coupling features that permit the first, second, third, and fourth buttons 61, 63, 64, and 66 to control movement of the containment tube 20, the grasping wire 22, the fork 30, and the retaining arm 50, respectively, in any relative orientation of the proximal portion 80 to the distal portion 81 of the handle. Each of the coupling features includes a first portion 90a, 90b, 90c, or 90d (collectively, the first portions 90) that is attached or rotationally fixed to a corresponding one of the buttons and rotationally fixed to the proximal portion 80 of the handle 60, and a second portion 91a, 91b, 91c, or 91d (collectively, the second portions 91) that is engagable with a corresponding one of the first portions and rotationally fixed to the distal portion 81 of the handle. Each first portion 90 is coupled to a corresponding linked element at the distal portion 14 of the catheter assembly 12 (one of the containment tube 20, the grasping wire 22, the fork 30, and the retaining arm 50) via one or more linkages, such that movement of the first portion along the longitudinal axis of the handle 60 actuates the respective linked element. Each second portion 91 extends at least partially around the circumference of an inner shaft 19 affixed to the outer shaft 16 and extending into the proximal portion 80 of the handle 60.

The first button 61 is operatively connected to the first portion 90a which has a circumferential recess 92a therein. The first portion 90a is engaged with the second portion 91a such that a circumferential rib 93a of the second portion is engaged in the circumferential recess 92a, thereby translationally fixing the first and second portions together while permitting rotation of the first and second portions relative to one another. When the first button 61 is moved in a direction of the longitudinal axis of the handle 60 along with the first portion 90a operatively connected thereto, the second portion 91a slides along the inner shaft 19 with the first portion in the direction of the longitudinal axis. When the proximal portion 80 of the handle 60 is rotated relative to the distal portion 81, the rib 93a of the second portion 91a rotates within the recess 92a of the first portion 90a, and the rib remains engaged in the recess, thereby permitting the first button 61 to control longitudinal movement of the containment tube 20 no matter what rotational orientation the first button has relative to the outer tube 16.

The second button 63 is operatively connected to the first portion 90b which has a circumferential recess 92b therein. The first portion 90b is engaged with the second portion 91b such that a circumferential rib 93b of the second portion is engaged in the circumferential recess 92b, thereby translationally fixing the first and second portions together while permitting rotation of the first and second portions relative to one another. The first and second portions 90b and 91b function in the same way as the first and second portions 90a and 91a described above, thereby permitting the second button 63 to control longitudinal movement of the grasping wire 22 no matter what rotational orientation the second button has relative to the outer tube 16.

The third button 64 is operatively coupled to the first portion 90c which has a circumferential recess therein (not shown). The first portion 90c is engaged with the second portion 91c such that a circumferential rib of the second portion (not shown) is engaged in the circumferential recess, thereby translationally fixing the first and second portions together while permitting rotation of the first and second portions relative to one another. The first portion 90c is rotationally fixed to the third button 64 and coupled thereto by linkages 94 that translate linear motion of the third button 64 in a first longitudinal direction into linear motion of the first portion in a second longitudinal direction opposite from the first longitudinal direction.

When the third button 64 is moved in a first longitudinal direction of the handle 60, the first portion 90c operatively coupled thereto is moved in a second longitudinal direction opposite from the first longitudinal direction, and the second portion 91c slides along the inner shaft 19 with the first portion in the second longitudinal direction. When the proximal portion 80 of the handle 60 is rotated relative to the distal portion 81, the rib of the second portion 91c rotates within the recess of the first portion 90c, and the rib remains engaged in the recess, thereby permitting the third button 64 to control movement of the fork 30 no matter what rotational orientation the third button has relative to the outer tube 16.

The fourth button 66 is operatively coupled to the first portion 90d which has a movable rib 95. The first portion 90d is engagable with the second portion 91d such that the movable rib 95 is engagable with first and second circumferential recesses 96a and 96b of the second portion, such that when the movable rib is engaged in one of the recesses 96, the first and second portions are translationally fixed together while permitting rotation of the first and second portions relative to one another. The first portion 90d is rotationally fixed to the fourth button 66 and coupled thereto by linkages 97 that translate linear motion of the fourth button generally in the direction of the longitudinal axis of the handle 60 into linear motion of the first portion in a direction parallel to the longitudinal axis.

The movable rib 95 of the first portion 90d is initially engaged with the first recess 96a of the second portion 91d. When the fourth button 66 is actuated for a first time to release the first clip 55a, the first portion 90d coupled thereto is moved in a proximal direction parallel to the longitudinal axis of the handle 60, and the second portion 91d slides along the inner shaft 19 with the first portion in the proximal direction. When the first portion 90d reaches its proximalmost position, a spring element returns the first portion and the fourth button 66 to their initial positions, and the movable rib 95 disengages from the first recess 96a and engages with the second recess 96b. When the fourth button 66 is actuated for a second time to release the second clip 55b, the first portion 90d coupled thereto is moved in the proximal direction parallel to the longitudinal axis of the handle 60, and the second portion 91d slides further along the inner shaft 19 with the first portion in the proximal direction.

When the proximal portion 80 of the handle 60 is rotated relative to the distal portion 81, the movable rib 95 of the first portion 90d rotates about the inner shaft 19 within the either the first recess 96a or the second recess 96b of the second portion 91d, and the movable rib remains engaged in the recess 96a or 96b, thereby permitting the fourth button 66 to control movement of the retaining arm 50 no matter what rotational orientation the fourth button has relative to the outer tube 16.

A safety rod 75a may extend through the handle 60 along an axis that is transverse to the longitudinal axis of the handle. The safety rod 75a may be slidable along the transverse axis between a locked position (not shown) in which an end (not shown) of the safety rod protrudes from a right-side surface 60a of the handle 60, and an unlocked position (FIG. 5A) in which an end 76 of the safety rod protrudes from a left-side surface 60b of the handle. In the locked position, the safety rod 75a prevents actuation of the fourth button 66 by engaging a locking tab 75b on the safety rod into either the first recess 96a or the second recess 96b of the second portion 91d, thereby preventing linear motion of the second portion 91d. In the unlocked position, the safety rod 75a frees the fourth button 66 for actuation by disengaging the locking tab 75b from either the first recess 96a or the second recess 96b of the second portion 91d, thereby permitting linear motion of the second portion 91d.

When the proximal portion 80 of the handle 60 is rotated relative to the distal portion 81, the locking tab 75b of the of the safety rod 75a rotates about the inner shaft 19 within either the first recess 96a or the second recess 96b of the second portion 91d, and the locking tab remains engaged in the recess 96a or 96b, thereby preventing actuation of the fourth button 66 no matter what rotational orientation the safety rod has relative to the outer tube 16.

To use the device 10 for transcatheter gathering of heart valve leaflet tissue, a user may first actuate the fourth button 66 of the handle 60 to retract the fingers 51 of the retaining arm 50 proximally of the gaps 42a and 42b between the anvil portions 40a, 40b, and 40c. The clips 55a and 55b may then be loaded into the respective gaps 42a and 42b, and the fourth button 66 may be released. The retaining arm 50 can be moved distally until the fingers 51 thereof cover the clips 55a and 55b and hold them in place.

Next, the distal portion 14 of the catheter assembly 12 may be inserted into a patient through the apex of the heart, for example, into the left ventricle, so that the distal portion is located close to the posterior leaflet 2 and the anterior leaflet 3 of the mitral valve 1.

Then, the fork 30 may be moved from the tissue-capturing position (FIG. 4A) to the open position (FIG. 4B) by sliding the third button 64 distally from an initial position (shown in FIG. 5A) to a distal position (not shown). The distal movement of the third button 64 pivots the fork 30 so that the ends 32 of the tines 31 move away from the closed side 41 of the outer tube 16 and away from the anvil 40.

Then, the distal portion 14 of the catheter assembly 12 may be moved so that the distal edge 17 of the outer tube 16 extends above the coaption line 5 of the mitral valve 1, and so that the first clip 55a is positioned near the coaption line, with the open side of the outer tube 16 facing the posterior leaflet 2 (alternatively, if the anterior leaflet 3 is being repaired, the open side of the outer tube may face the anterior leaflet). In a particular embodiment, the distal edge 17 of the outer tube 16 may be guided to a position above the coaption line 5 using the assistance of three-dimensional echocardiography to visualize the outer tube or other components of the catheter assembly 12.

Then, the containment tube 20 may be deployed by sliding the first and second buttons 61 and 63 together distally from an initial position to a deployed position. The distal movement of the first button 61 moves the tip 21 of the containment tube 20, and with it the grasping wire 22, toward the distal end 17 of the outer tube 16, such that the tip 21 extends above the coaption line 5.

The hook 24 may then be deployed to an extended position by sliding the second button 63 distally relative to the first button 61 from an initial position to a deployed position (shown in FIG. 4B). The distal movement of the second button 63 relative to the first button 61 moves the distal portion 23 of the grasping wire 22 out of the containment tube 20. No longer being constrained by the containment tube 20, the distal portion 23 of the grasping wire 22 may assume the curved shape of the hook 24.

Next, the hook 24 may be partially retracted against the tissue of the posterior leaflet 2 by sliding the first and second buttons 61 and 63 together proximally. The proximal movement of the first and second buttons 61 and 63 partially retracts both the containment tube 20 and the grasping wire 22, without relative movement between them, such that the hook engages against the upper surface 6 of the posterior leaflet 2 and pulls tissue of the leaflet into the space 43 between the anvil 40 and the tines 31 of the fork 30 (FIG. 4B).

Some of the leaflet tissue below the coaption line 5 may extend into the pocket 36 between the containment tube 20 and the tines 31 of the fork 30. As described above, the gathering of tissue into the pocket 36 within the concave C-shaped portion 35 of the tines 31 may help prevent captured leaflet tissue from sliding out from the space 43 between the tines and the closed side 41 of the outer tube 16 as the fork 30 clamps tissue against the anvil 40. The presence within the C-shaped portion 35 of a generally proximal-facing surface 29 may help interfere with and retain tissue in the pocket 36 that may otherwise begin to slide out from the space 43 as the fork 30 clamps tissue against the anvil 40.

The tissue captured in the space 43 may be clamped between the anvil 40 and the tines 31 of the fork 30 by sliding the third button 64 proximally from the open position to the tissue-capturing position. The proximal movement of the third button 64 pivots the fork 30 so that the ends 32 of the tines 31 move toward the closed side 41 of the outer tube 16 and toward the anvil 40.

Continued movement of the tines 31 of the fork 30 toward the anvil 40 will force the captured tissue 9 into the space 33 between the tines 31, and into the spaces between the tines and the closed side 41 of the outer tube 16. A W-shaped pleat 8 (FIG. 3) will thus be formed in the captured tissue 9, with the raised center portion of the W overlying the anvil 40, and the two lower portions of the W lying between the tines 31 and the closed side 41 of the outer tube 16.

With the tissue captured, the retaining arm 50 may be retracted to a first deployment position by releasing the safety rod 75a and actuating the fourth button 66. The retaining arm 50 may be retracted until the fingers 51 thereof are proximal of the distal gap 42a in the anvil 40 (FIG. 4C). At this juncture, the fingers 51 will no longer overlie the first clip 55a, such that the two prongs 56 of the first clip will be free to spring away from the closed surface 41 of the outer tube 16 and become embedded in the captured tissue 9 of the posterior leaflet 2, thereby securing the tissue in the pleated form.

If desired, the retaining arm 50 may optionally be retracted to a second deployment position by again actuating the fourth button 66 to deploy the second clip 55b. The retaining arm 50 may be further retracted until the fingers 51 thereof are proximal of the proximal gap 42b in the anvil 40 (FIG. 4C). At this juncture, the fingers 51 will no longer overlie the second clip 55b, such that the two prongs 56 of the second clip will be free to spring away from the closed surface 41 of the outer tube 16 and become embedded in the captured tissue 9 of the posterior leaflet 2.

After one or both of the clips 55a and 55b have been adequately secured in the tissue of the posterior leaflet 2, the device 10 may be withdrawn from the patient. To withdraw the device 10, the hook 24 may first be withdrawn from engagement with the posterior leaflet 2 by retracting the second button 63 relative to the first button 61. This action causes the hook 24 to straighten as the grasping wire 22 retracts into the containment tube 20.

Next, the clips 55a and 55b may be withdrawn from the respective gaps 42a and 42b in the anvil 40 by moving the third button 64 distally, thereby moving the fork from the tissue-capturing position to the open position. The distal movement of the third button 64 pivots the fork 30 so that the ends 32 of the tines 31 move away from the closed side 41 of the outer tube 16 and away from the anvil 40, and the captured tissue 9 and the clips 55a and 55b are moved away from the anvil along with the tines.

Once the clips 55a and 55b are withdrawn from the respective gaps 42a and 42b, the user may begin to withdraw the catheter assembly 12 from the patient, thereby pulling the tines 31 of the fork 30 out of the clips. After the fork 30 has disengaged from within the clips 55a and 55b, the prongs of the clips may become more tightly embedded in the posterior leaflet 2, such that the two prongs may cross one another, thereby allowing the clip to extend along an arc that is greater than 360 degrees. Finally, the catheter assembly 12 may be fully withdrawn from the patient through the apex of the heart.

Portions of the procedure described above may be performed twice to individually apply the first clip 55a and the second clip 55b to separate locations within the mitral valve, on the same leaflet or on different leaflets. For example, the first clip 55a may be applied to the posterior leaflet 2, the proximal and distal portions 80, 81 of the handle 60 may be rotated relative to one another so that the open side of the outer tube 16 rotates 180° and faces the anterior leaflet 3, and the second clip 55b may then be applied to the anterior leaflet.

After the device 10 is withdrawn from the patient, if one or both of the clips 55a and 55b were misfired and are not engaged in leaflet tissue, one or both of the clips may be withdrawn from the patient. Optionally, a suture may extend around each of the clips 55, and the ends of each suture may be attached to a respective rotatable spool within the catheter assembly 12 (not shown) so that one or both of the clips may be retrieved after withdrawal of the device 10 from the patient. A recessed channel 44 may be provided between the retaining arm 50 and the closed side 41 of the outer tube to permit routing of the suture proximally through the outer tube.

In use, after the clips 55a and 55b have been released and the user wants to retrieve a clip from the patient, the user may grasp both ends of the respective suture and pull until the clip is withdrawn from the patient. If the clip has been placed properly and is to remain in place in the leaflet tissue, the user may grasp only one end of the suture and pull the one end until the other end is pulled out of the clip.

In the devices shown in the figures, particular structures are shown that are adapted to gather, secure, and repair heart valve leaflet tissue. The invention also contemplates the use of any alternative structures for such purposes, including structures having different lengths, shapes, and configurations. For example, although the capture tool is shown in the form of a grasping wire 22, the capture tool may take other forms, including for example, a pincer-like structure such as a clamp. Although the clamping member is shown in the form of a fork 30, the clamping member may have other configurations, such as an arm having a curved surface such that outer edges of the arm can serve as tines, a lattice structure, or any other structure capable of retaining leaflet tissue against the anvil 40 and the closed surface 41 of the outer shaft 16. The tissue support is shown as an anvil 40, but may take other forms, such as a corrugated surface, a set of pins extending from the closed surface 41 of the outer shaft 16, or any other shape that can guide leaflet tissue into a desired shape onto which one or more clips 55 can be attached.

In another example, although the catheter assembly is described as being controllable by the movement of a particular configuration of buttons 61, 63, 64, and 66 of a handle 60, any mechanisms that are adapted to control the movement and deployment of the containment tube, grasping wire, fork, and clips may be used. Furthermore, although the grasping wire 22 is shown as having a hook 24, the distal portion of the grasping wire may have any shape or configuration that may be adapted to grasp a target portion of valve leaflet tissue and help to capture such tissue inside or adjacent the outer tube such that one or more clips may be applied to the captured tissue.

Moreover, although the fork 30 is described as having two tines 31 that cooperate with the anvil 40 to capture leaflet tissue and form same into a W-shaped pleat, the invention contemplates forks having any number of tines cooperating with any number of anvils to form any number of pleats in the captured tissue. For example, a fork having a single tine may cooperate with two anvils that are laterally spaced apart from one another to form leaflet tissue into a pleat. It will be appreciated that the more pleats that are formed, the more the tissue of the valve leaflet can be tightened. In a particular embodiment, the tissue capture mechanism may include an outer tube 16 without an anvil portion extending from the inner surface 41 thereof, wherein the tines 31 of the fork 30 are adapted to capture leaflet tissue in a single contiguous space defined within the outer tube, such that a portion of the inner surface of the outer tube may serve as an anvil portion. In such an embodiment without an anvil portion extending from the inner surface 41 of the outer tube 16, the hook 24 and the containment tube 20 may serve as an anvil portion to cooperate with the fork 30 to form leaflet tissue into a W-shaped pleat.

Although the device 10 is shown as being adapted to apply one or two clips 55 onto one or both of the posterior leaflet 2 and the anterior leaflet 3, the invention contemplates devices that are adapted to apply more than two clips to the leaflet tissue during a single insertion of the device into a patient. For example, the gaps 42a and 42b between the anvil portions may be sufficiently large to accommodate a plurality of clips 55 in side-by-side relationship. In such an embodiment, while leaflet tissue is captured within the outer tube 16, the retaining arm 50 may be retracted to more than two positions to apply more than two clips 55 to the tissue at more than two locations. Furthermore, the invention contemplates devices that are adapted to apply only a single clip 55 to the leaflet tissue during a single insertion of the device into a patient. In such an example, the device 10 may have a tissue support in the form of an anvil having only distal and proximal portions, with a single gap defined between the distal and proximal portions in which a clip 55 may be loaded.

Although the various delivery devices have been described herein in connection with tightening the posterior leaflet of a mitral valve, all of the delivery devices may be used on other heart valve leaflets, such as the anterior leaflet of the mitral valve (which is shown in FIG. 1 as the anterior leaflet 3), or on any other tissue of the body for which a reduction in the length of the tissue would be beneficial.

Although the invention herein has been described with reference to particular embodiments in which the catheter assembly is inserted into the patient through the apex of the heart (i.e., transapical insertion), it is to be understood that the invention contemplates embodiments in which the catheter assembly extends through a portion of the vasculature of the patient to reach the heart, for example, through a transfemoral or subclavian artery. In such embodiments, some of the device components may have to be oriented in a different direction to that described herein. For example, the invention contemplates embodiments in which the distal portion of the catheter assembly approaches the mitral valve from the upstream side as well as from the downstream side of the valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A device for transcatheter gathering of tissue of a heart valve leaflet, the device comprising:
    an elongated tube extending in a longitudinal direction;
    a capture tool moveable in the tube between a retracted position and an extended position;
    a tissue support located within a distal portion of the tube;
    a clamping member pivotable in the tube between an open position spaced from the tissue support and a closed position adjacent the tissue support, the clamping member having a flattened clamping portion and a C-shaped portion that defines a pocket therein, an open side of the C-shaped portion facing the tissue support, the capture tool and the clamping member being operable to gather and clamp tissue of the heart valve leaflet between the tissue support and the clamping member, such that the clamped tissue has a gathered configuration;
    a releasable clip adapted to be applied to the clamped tissue for holding the clamped tissue in the gathered configuration; and
    a retaining arm moveable between a distal position for retaining the clip and a proximal position for releasing the clip for application to the clamped tissue.

2. The device of claim 1, wherein a distal portion of the clamping member has a fork shape.

3. The device of claim 2, wherein the distal portion of the clamping member has two tines having respective ends that are spaced apart from one another by an internal gap.

4. The device of claim 1, further comprising an operating handle having an actuating member adapted to control pivoting of the clamping member between the open and closed positions.

5. The device of claim 1, wherein the device includes two releasable clips adapted to be applied to the clamped tissue for holding the clamped tissue in the gathered configuration, and wherein each clip is biased from an open condition to a clamping condition, the retaining arm in the distal position holds the clips in the open condition, and the retaining arm in the proximal position releases the clips for application to the clamped tissue.

6. The device of claim 5, wherein the tissue support includes first, second, and third bodies spaced apart in the longitudinal direction, and wherein, when the clips are held in the open condition by the retaining arm, a first one of the clips is located between the first and second bodies, and a second one of the clips is located between the second and third bodies.

7. The device of claim 5, wherein movement of the retaining arm from the distal position to an intermediate position releases a first one of the clips, and wherein movement of the retaining arm from the intermediate position to the proximal position releases a second one of the clips.

8. The device of claim 1, further comprising an operating handle having an actuating member adapted to control movement of the retaining arm between the distal position and the proximal position.

9. The device of claim 8, wherein the device includes two releasable clips adapted to be applied to the clamped tissue for holding the clamped tissue in the gathered configuration, and wherein a first actuation of the actuating member moves the actuating member from the distal position to an intermediate position to release a first one of the clips, and a second actuation of the actuating member moves the actuating member from the intermediate position to the proximal position to release a second one of the clips.

10. The device of claim 1, wherein the capture tool includes a grasping wire slidably disposed in a containment tube, and wherein a distal portion of the grasping wire is adapted to change from a linear shape to a hook shape when the distal portion of the grasping wire is extended out from the containment tube.

11. A device for transcatheter gathering of tissue of a heart valve leaflet, the device comprising:
    an elongated tube extending in a longitudinal direction;
    a capture tool moveable in the tube between a retracted position and an extended position;
    a tissue support located within a distal portion of the tube;
    a clamping member pivotable in the tube between an open position spaced from the tissue support and a closed position adjacent the tissue support, the capture tool and the clamping member being operable to gather and clamp tissue of the heart valve leaflet between the tissue support and the clamping member, such that the clamped tissue has a gathered configuration;
    a releasable clip adapted to be applied to the clamped tissue for holding the clamped tissue in the gathered configuration;
    a retaining arm moveable between a distal position for retaining the clip and a proximal position for releasing the clip for application to the clamped tissue; and
    an operating handle having a distal portion that is affixed to the elongated tube and a proximal portion that is rotatable relative to the distal portion about a longitudinal axis of the handle.

12. The device of claim 11, wherein the operating handle has an actuating member movable between a first position and a second position, the proximal portion of the operating handle being rotationally locked to the distal portion of the operating handle when the actuating member is in the first position, and the proximal portion of the operating handle being released for rotation relative to the distal portion of the operating handle when the actuating member is in the second position.

13. The device of claim 12, wherein the actuating member includes a spring element that biases the actuating member to the first position.

14. The device of claim 11, wherein the device includes two releasable clips adapted to be applied to the clamped tissue for holding the clamped tissue in the gathered configuration, and wherein movement of the retaining arm from the distal position to an intermediate position releases a first one of the clips, and wherein movement of the retaining arm from the intermediate position to the proximal position releases a second one of the clips.

15. A transcatheter method of gathering tissue of first and second heart valve leaflets, the method comprising:
    inserting an elongated catheter assembly to a position adjacent the first heart valve leaflet, the catheter assembly extending from an operating handle in a longitudinal direction and including a capture tool moveable between a retracted position and an extended position, a tissue support, a clamping member pivotable between an open position spaced from the tissue support and a closed position adjacent the tissue support, and a retaining arm moveable between a distal position for retaining two clips and a proximal position for releasing the clips, the operating handle having a distal portion that is affixed to the catheter assembly and a proximal portion that is rotatable relative to the distal portion about a longitudinal axis of the handle;

moving the capture tool from the retracted position to the extended position;

pivoting the clamping member from the closed position to the open position adjacent the first heart valve leaflet, such that a distal portion of the clamping member moves laterally away from the tissue support in a direction transverse to the longitudinal direction;

manipulating the catheter assembly so that tissue of the first heart valve leaflet is positioned between the tissue support and the clamping member;

partially retracting the capture tool from the extended position toward the retracted position to gather an additional amount of tissue of the first heart valve leaflet between the tissue support and the clamping member;

pivoting the clamping member from the open position toward the closed position so as to clamp a substantial portion of the gathered tissue of the first heart valve leaflet between the tissue support and the clamping member, such that the distal portion of the clamping member moves laterally toward the tissue support in the direction transverse to the longitudinal direction, the clamped tissue having a gathered configuration;

moving the retaining arm from the distal position to an intermediate position to apply a first one of the clips from the catheter assembly to the clamped tissue so as to hold the clamped tissue substantially in the gathered configuration;

rotating the catheter assembly and the distal portion of the operating handle relative to the proximal portion of the operating handle; and moving the retaining arm from the intermediate position to the proximal position to apply a second one of the clips from the catheter assembly to the tissue of the second heart valve leaflet.

16. The method of claim 15, wherein each clip is biased from an open condition to a clamping condition and the retaining arm holds the clips in the open condition, and wherein the step of moving the retaining arm from the distal position to the proximal position releases the clips for movement to the clamping condition.

17. The method of claim 15, wherein the operating handle having an actuating member moveable in opposite directions, and wherein the step of pivoting the clamping member from the closed position to the open position includes moving the actuating member in a first one of the opposite directions.

18. A transcatheter method of gathering tissue of a heart valve leaflet, the method comprising:

inserting an elongated catheter assembly to a position adjacent the heart valve leaflet, the catheter assembly extending in a longitudinal direction and including a capture tool moveable between a retracted position and an extended position, a tissue support, a clamping member pivotable between an open position spaced from the tissue support and a closed position adjacent the tissue support, and a retaining arm moveable between a distal position for retaining two clips and a proximal position for releasing the clips;

moving the capture tool from the retracted position to the extended position;

pivoting the clamping member from the closed position to the open position adjacent the heart valve leaflet, such that a distal portion of the clamping member moves laterally away from the tissue support in a direction transverse to the longitudinal direction;

manipulating the catheter assembly so that tissue of the heart valve leaflet is positioned between the tissue support and the clamping member;

partially retracting the capture tool from the extended position toward the retracted position to gather an additional amount of tissue of the heart valve leaflet between the tissue support and the clamping member;

pivoting the clamping member from the open position toward the closed position so as to clamp a substantial portion of the gathered tissue of the heart valve leaflet between the tissue support and the clamping member, such that the distal portion of the clamping member moves laterally toward the tissue support in the direction transverse to the longitudinal direction, the clamped tissue having a gathered configuration;

moving the retaining arm from the distal position to an intermediate position to apply a first one of the clips from the catheter assembly to the clamped tissue so as to hold the clamped tissue substantially in the gathered configuration; and moving the retaining arm from the intermediate position to the proximal position to apply a second one of the clips from the catheter assembly to the clamped tissue.

19. The method of claim 18, wherein the catheter assembly further includes an operating handle having an actuating member actuatable in a first direction, wherein the step of moving the retaining arm from the distal position to the intermediate position is performed by actuating the actuating member a first time, and wherein the step of moving the retaining arm from the intermediate position to the proximal position is performed by actuating the actuating member a second time.

20. The method of claim 18, wherein the capture tool includes a grasping wire slidably disposed in a containment tube, the method further comprising sliding a distal portion of the grasping wire out from the containment tube so that the distal portion of the grasping wire changes from a linear shape to a hook shape.

* * * * *